(12) United States Patent
Olds

(10) Patent No.: US 11,995,696 B2
(45) Date of Patent: May 28, 2024

(54) METHOD FOR IMPROVING SERVICE OUTCOMES USING ARTIFICIAL INTELLIGENCE TECHNIQUES

(71) Applicant: i2i LLC, Austin, TX (US)

(72) Inventor: Glenn Olds, Austin, TX (US)

( * ) Notice: Subject to any disclaimer, the term of this patent is extended or adjusted under 35 U.S.C. 154(b) by 78 days.

(21) Appl. No.: 17/226,873

(22) Filed: Apr. 9, 2021

(65) Prior Publication Data

US 2022/0327582 A1 Oct. 13, 2022

(51) Int. Cl.
*G06Q 30/02* (2023.01)
*G06Q 30/0203* (2023.01)
*G06Q 30/0282* (2023.01)
*G16H 80/00* (2018.01)

(52) U.S. Cl.
CPC ..... *G06Q 30/0282* (2013.01); *G06Q 30/0203* (2013.01); *G16H 80/00* (2018.01)

(58) Field of Classification Search
CPC ................. G06Q 30/02; G16H 80/00
See application file for complete search history.

(56) References Cited

U.S. PATENT DOCUMENTS

| | | | | |
|---|---|---|---|---|
| 2002/0156743 A1* | 10/2002 | DeTreville | ............. | G06Q 30/02 705/57 |
| 2009/0112623 A1* | 4/2009 | Schoenberg | ........... | G06Q 10/02 705/2 |
| 2014/0136443 A1* | 5/2014 | Kinsey, II | .......... | G06Q 30/0282 705/347 |
| 2014/0288951 A1* | 9/2014 | Zielinski | ................ | G16H 15/00 705/2 |
| 2014/0316812 A1* | 10/2014 | Hathorn | ................. | G16H 40/20 705/3 |
| 2016/0239778 A1* | 8/2016 | Suneja | ............. | G06Q 10/06316 |
| 2017/0351830 A1* | 12/2017 | Burger | .................. | G16H 80/00 |
| 2019/0108909 A1* | 4/2019 | Lee | .................... | G06Q 10/1095 |
| 2019/0311301 A1* | 10/2019 | Pyati | ..................... | G06F 16/901 |
| 2019/0333613 A1* | 10/2019 | Zaidi | ..................... | G16H 40/63 |
| 2020/0185089 A1* | 6/2020 | Karam | .................... | G06F 16/29 |
| 2020/0311586 A1* | 10/2020 | Sandstrom | ......... | G06Q 30/0278 |

* cited by examiner

*Primary Examiner* — Vincent M Cao

(57) ABSTRACT

This document presents a system and method of applying machine learning and deep learning techniques to improve service outcomes by allowing for a novel method of matching service providers with clients. This system and method involves collecting data on the expressed and latent preferences and attributes of both a service provider and a client as well as outcome data regarding outcome improvement and the quality of the match. By using a deep learning approach to analyze this data and identify latent variables and non-linear relationships, this system is able to predict which pairing of service providers and clients will most likely lead to the desired outcomes. This system and method can be applied to any professional relationship where personality factors and relationship compatibility are predictive of desired outcomes. These include but are not limited to clinician-patient, educator-student, professional-client and salesperson-customer relationships.

20 Claims, 6 Drawing Sheets

METHOD FOR IMPROVING SERVICE OUTCOMES USING ARTIFICIAL INTELLIGENCE TECHNIQUES

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Matching professional service providers with clients is typically a manual process. There are matching services that provide some surveys that attempt to match characteristics between a person seeking professional services, such as psychiatric or psycho-therapeutic assistance, and a professional provider, whether an individual clinician or a practice group. These surveys are often long and complicated and depend upon the person providing truthful answers to the questions posed. There are also tests that have been created to specifically determine individual characteristics for the person taking the test. These test results, along with the completed surveys, are often evaluated manually by a service provider in an attempt to arrive at a match between the person seeking the services and those providing such services. A manual evaluation can be very accurate, or it can be inaccurate, due to a number of factors, but there are few checks to determine whether a match is beneficial prior to an individual engaging the professional and working together to discover if the match is a good one.

Software systems exist to attempt to arrive at better matches based upon historic observations in addition to individual survey and test results. These systems are only as capable as the data supplied for evaluation and rarely have the ability to look forward to predict future behavior for new individuals using the system for a professional match. Broader and more robust data stores assist in the evaluation by the software system and provide greater confidence in the matches made based upon historic data trends. Statistical analysis systems may be employed to facilitate new matches based upon historic trends for particular clinicians and practice groups. However, once again, datasets available to any particular clinician or practice group may be limited to data collected and stored by the particular practice group or clinician. Characteristics of the clinician or service provider may not always be updated or accurate as a practice group or individual practice grows over time. Integrated techniques for combined dataset analysis, individual surveys, updated clinician information, and software managed deep learning to improve clinical results for individuals, clinicians, and practice groups may not be readily found causing frustration with existing systems for both users and providers of such services.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
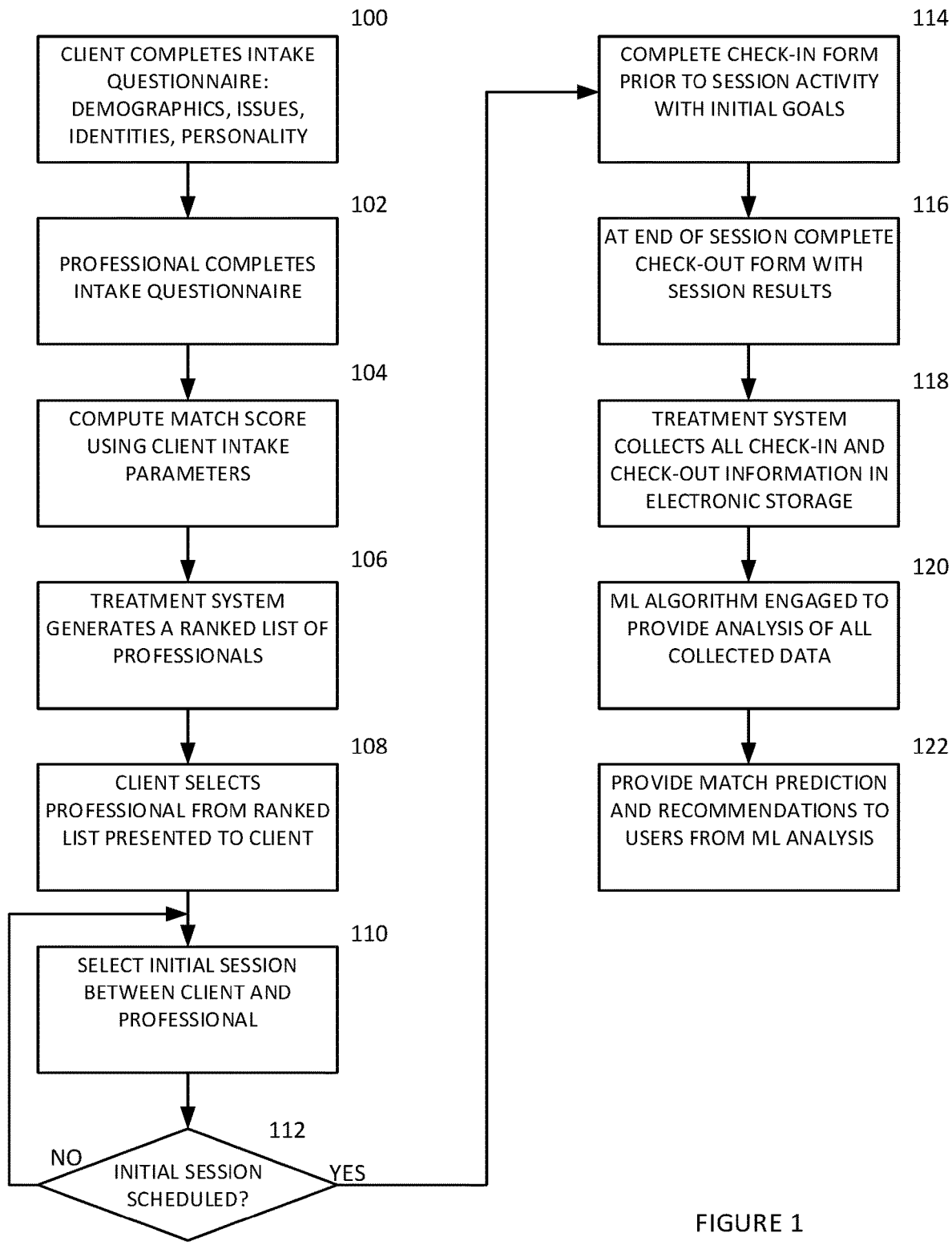
FIG. 1 is a flow diagram for matching a client with a professional service provider consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "service provider" is used in this document to refer to any individual or group who provides a service to a service recipient. Service providers include but are not limited to, clinicians, clinics, professionals, salespersons, educators and mentors.

The term "service recipient" is used in this document to refer to any individual or group who receives a service to a service provider. Service recipients include but are not limited to, patients, clients, customers and students.

The innovation herein described presents a system and method for collecting information and deriving insights from AI methods to improve the desired service outcomes that result from a relationship between a service provider and a service recipient. Improving service outcomes may require one or more of numerous techniques and methodologies that will be herein presented.

To assist with improving desired outcomes between service providers and service recipients, the service outcome optimization system may collect information and use artificial intelligence techniques in order to discover additional latent features such as personality characteristics, experiences, concerns, identities, preferences, and abilities for service providers and the service recipients. Providers and recipients are matched based on these expressed and latent features and then before, during and/or after the provision of a service, the system collects data based upon the desired outcomes of the relationship. This outcome data may assist with improving the matching of future providers and recipients through the use of machine learning and deep learning algorithms that analyze and compare collected data to derive similarities and differences and make predictions about the likelihood of achieving successful service outcomes that would not be readily apparent only from a single sample or single encounter between any provider and/or recipient or based only on a provider or recipient's expressed characteristics.

In an embodiment, the system may also use crowd sourcing of data on a user's personality and preferences, collecting information from broad swaths of clients both past and current as well as from other individuals who have personal experience with the user. This data is used to improve user profiles for recommendations and to improve user profiles for a better personality and preference fit between users, To achieve these goals the system may use machine learning and deep learning algorithms to create insights from the collected data for users. In a non-limiting example, these insights may include the ability for clinicians to understand what they are really good at as opposed to what they believe they are good at. Additionally, these insights may provide for automated clinical supervision for clinicians, and may improve clinician hiring through gathering client and clinician personality to transition to client driven hiring. The collected data and data analysis may also reduce bias and support client driven hiring of clinicians for true expertise as a component of predicting latent ability of a potential hire. This data analysis assists in making hiring decisions based on predictions of which candidates will best meet the needs and lead to the best outcomes for an organization's current and future clients and enable insight driven referrals.

In an embodiment, the service outcome optimization system may apply statistical, analytical, machine learning and/or deep learning techniques to improve outcomes by establishing a novel means for matching service providers with service recipients. The service outcome optimization system may collect and infer data on the expressed and latent preferences and attributes of both a service provider and a service recipient as well as outcome data regarding outcome improvement experienced over time and the quality of the match between the service provider and the service recipient. A machine learning approach, including analytical algorithms and other deep learning methods, may be used to analyze the collected data for success in matching characteristics and pairings between service providers and service recipients. The machine learning process may then predict, for future engagements and optimizing current engagements, which pairing of a service provider and service recipient will most likely lead to a desired service outcome. In an embodiment, the service outcome optimization system may collect data through crowdsourcing of profile information to improve the accuracy of user profiles. Improvement of all user profiles may be enhanced through the assumption that individuals with a knowledge of a user's personality are likely to provide a useful assessment of a user's personality beyond what the user is able to provide for themselves.

In a non-limiting example, the accuracy of such appraisals may be further improved by soliciting and collecting feedback from many former and current service recipients who have worked with the service provider. This crowdsourced service provider profile information may be used to provide greater confidence in the accuracy of the service provider's profile when compared to profile generated only through self-appraisal.

In an embodiment, the service outcome optimization system may utilize machine learning techniques including deep learning, artificial intelligence, and other machine learning algorithms and methods to generate insights for service providers such as, in non-limiting examples, clinicians, professionals, educators, and salespersons, in order to identify and present previously unidentified strengths and/or areas for growth in their field of endeavor. The automated supervision and feedback provided by this process can be used to augment traditional training or supervisory relationships. Through feedback and unique interpersonal insights provided by this method, a supervisor is better able to target training experiences to help a professional to make improvement in previously unidentified areas of weakness. The deep learning algorithms may access all input data from service providers, service recipients and crowdsourced information to discover previously unknown connections, strengths, weaknesses, and conditional actions for individuals referenced within the collected data. This information may be used by the deep learning algorithms to predict future advantageous combinations of service providers and service recipients, and provide recommendations and feedback regarding the success of the match and the outcomes of the match to a supervisor or manager of the service provider. The method also provides the service provider and the supervisor with direct feedback regarding the actual impact of professional development experiences on service outcomes and the provider-recipient relationship. The deep learning algorithms may continue to utilize ongoing data inputs of results from provider-recipient relationships to improve the confidence in predictions and recommendations for future interactions.

In an embodiment, the service outcome optimization system may utilize machine learning/deep learning techniques as a method for insight generation for organizations regarding hiring decisions. Organizations may be provided with deep insights into the latent preferences of service recipients who are engaging with the organization, as well as an assessment of how well the professionals within the organization are meeting these latent needs. The service outcome optimization system is able to identify the ideal service provider for a service recipient. These insights may be broadened and presented as predictions and recommendations to help an organization make decisions regarding staffing needs. The process attempts to remove personal bias in hiring by first identifying the expressed and latent needs and preferences of incoming service recipients through analysis of historic data maintained by the service outcome optimization system, or, in the case of a new individual, ingesting information from the new individual and analyzing the new data in combination with historical data that may contain similarities or markers that are similar to the new individual's input data. Using the retained historic and currently input information, the algorithm may be able to identify the desired attributes of the perfect match between a service recipient, whether new or ongoing, and a service provider. As the service outcome optimization system begins making matches it is also continually assessing how well the organization is able to provide a service provider who closely meets the needs of the service recipient from among the current pool of available providers within the organization. This method of optimization, known as "service outcome driven hiring", allows employers to make hiring decisions with increased confidence that these decisions are optimally meeting the needs of their service recipients, improving the desired outcomes of the service relationship. These desired outcomes may include but are not limited to patient improvement, customer satisfaction, increased sales, subject mastery or goal completion.

In an embodiment, the service outcome optimization system may also provide a process for distributing referrals based on the latent preferences of an service recipient being referred to an individual or organization in order to improve outcomes for the service recipient and the service provider to whom the service recipient has been referred. The service outcome optimization method when applied to the task of distributing referrals, may use an initial statistics-based approach and then transition to a deep learning approach as the system collects additional data to predict performance based on the quality of the match between a service provider, such as a salesperson, clinician, educator, or other professional, and a service recipient, such as a patient, customer, student, or other client. This information, comprising predictions and recommendations, may then also be used as a decision-making tool for distributing referrals within organizations, directories, practices, and other professional organizations in order to optimize and maximize the desired outcome of the service relationship.

In an embodiment, the core application of the service outcome optimization system comprises applying Machine Learning technologies, both statistics-based and Deep Learning to match service recipients with service providers in order to improve a desired outcome. The desired outcome may depend on the nature of the service relationship and may include but is not limited to, an improved treatment outcome, an improvement in client retention, mastery of a new skill or subject or an improvement in relationships between a service provider and a service recipient. In this embodiment, the service outcome optimization system may collect a wide variety of data points, including but not limited to, clinical, clinician, survey, client, customer, assessment and/or patient information to discover expressed and latent characteristics, including personality characteristics, for both service providers and service recipients seeking the services of those providers. Artificial Intelligence approaches, including Machine Learning and Deep Learning algorithms, will then utilize all collected data, including historical data, survey data, assessment data, service outcome data (where available), and crowdsourced data, to optimize the matching of service providers with service recipients, and optimize the matching of service providers with organizations to realize improved outcomes in treatment, referrals and hiring.

In an embodiment, the service outcome system may use crowd sourcing of data from other individuals with knowledge of a user's personality to improve the accuracy of all user profiles.

In an embodiment, the service outcome optimization system may also use crowd sourcing of data, collecting information from broad swaths of service recipients both past and current to improve the profiles of service providers for recommendations to service recipients and organizations.

In a non-limiting example, where the service outcome optimization system is used in a clinical psychiatric environment, the service outcome optimization system may utilize Artificial Intelligence techniques including machine learning, artificial intelligence, and deep learning algorithms to create insights from the collected data for both clients and clinicians. The insights provided by the specified algorithms may include the ability for clinicians to understand what they are really good at as opposed to what they believe they are good at, may provide for automated clinical supervision for clinicians, may serve as a supervision tool for supervisors and managers, may improve clinician hiring, and may gather client and clinician personality information to transition to client driving hiring. This collected and analyzed data may also reduce bias in hiring and support client driven hiring of clinicians for true expertise and enable and optimize insight driven referrals.

Utilizing the Service Outcome Optimization System for Matching Therapists and Clients:

In an embodiment, when the service outcome optimization system is performing an analysis to match service providers with service recipients, the system must first gather information about the service recipient and create a Service Recipient Profile. To perform this action, a service recipient must create a profile through the user interface portal of the service outcome optimization system to create the profile. The service outcome optimization system may then request that the user then complete an intake questionnaire, or the system may collect customer-based profile information from public sources such as social media postings, job listing usage, real-estate listing usage, or other demographic and usage data to build a customer-based profile. In a non-limiting example, where the service outcome optimization system collects user information through an intake questionnaire, the intake questionnaire may consist of four sections "Demographics," "Issues," "Identities," and "Personality" which are defined herein as:

Demographics section: Collects information about the client such as age, education, marital status, geographic location and contact information.

Issues section: Includes questions about the client's needs and clinical concerns. Clients select the needs and issues for which they may be seeking assistance. For example, areas of concern might include depression, anxiety, procrastination, existential issues, among others. Clients are asked to rate each of these clinical concerns in response to the question: "How important is it to find a therapist with expertise in treating (insert clinical concern here)." Responses are recorded on a slider scale, discretized as floating point numbers from 0, no importance, to 1, most important, in increments of 0.01 with the midpoint at 0.5. The responses may be recorded as "Not very important" for low integer values, through "Somewhat important", for mid-range integer values, to "Extremely important", for high integer values.

Identities section: Includes questions about identities that are important to the client. These include questions about religion, sexuality, ethnicity and gender. Clients then are asked to rate each of their selected identities in response to the question: "How important is it to find a therapist who shares or has a deep understanding of (insert identity here) issues." Responses are recorded on a slider scale, discretized as floating point numbers from 0, no importance, to 1, most important, in increments of 0.01 with the midpoint at 0.5. The responses may be recorded as "Not very important" for low integer values through "Somewhat important", for midrange integer values, to "Extremely important", for high integer values.

Personality section: Includes two subsections. Subsection 1 includes general personality questions. These questions are answers on a slider discretized as floating point numbers from 0, no importance, to 1, most important, in increments of 0.01 with the midpoint at 0.5. These questions are designed to allow the client to express preferences. Subsection 2 uses semantic differential items. These are pairings of words or phrases that are opposites but which could also both be desirable traits in a therapist. In a non-limiting example, to facilitate the collection of this information the client may be shown the prompt: "I would prefer a therapist who is _____" and then shown a slider with "Supportive" on one end and "Challenging" on the other and the response to the prompt from the client is collected and stored in the data file associated with the client.

In an embodiment, therapists also complete an intake questionnaire that closely mirrors the one completed by clients. In a non-limiting example, clients may be asked to select all concerns that are motivating them to seek therapy. Therapists may be asked to select all concerns for which the therapist may have treatment experience and expertise. In a non-limiting example, a Therapist may be shown the prompt: "I would describe my therapeutic style as _____" and then also shown a slider with "Supportive" on one end and "Challenging" on the other for entry of their response. The Therapists response is collected and stored in a therapist profile data file associated with that particular Therapist.

In a non-limiting example, when calculating a match score for a single question the service outcome optimization system may compare the client's response to the responses of all therapist profiles. Since there will be a symmetry between the client's answer and the therapist's answer, initially, a statistics based matching algorithm is utilized that can calculate the root mean squared difference between the client's preference for an attribute and a therapist's self-description of an attribute. This process assumes that a stronger agreement in the preference of a client and the self-reported agreement to that preference by a therapist results in a stronger match. This statistics-based approach is one method for addressing the "cold start" problem encountered in ML/deep learning systems where initially there is inefficient training data. Later on, once enough training data has been collected, the service outcome optimization system will transition from using a simplistic statistics-based matching approach to a machine learning and deep learning approach to better match a client with a therapist based on the identification of previously unidentified latent variables and through the discovery of non-linear relationships between variables.

In a non-limiting example, the match score between any client and therapist pair is computed using three components; personality, issues and identities, and competence. The Issues and Identities score represents the degree of match between the client's needs and the therapist's areas of expertise. The personality score represents the degree of match between a client's preferences regarding therapist personality and a therapist's self-description of their therapeutic style. The competence score is calculated based on outcome data and is an overall measure of a therapist's efficacy with a wide range of clients.

In an embodiment, all parameters utilized in the analysis and calculation of the match score between any client and therapist pair are first collected as input on a slider ranging between 0.01, not important, to 1.0, very important, with the midpoint at 0.5. The sliders are then normalized and discretized as floating point numbers from 0, no importance, to 1, most important, in increments of 0.01 with the midpoint at 0.5 as shown in previous discussion.

In an embodiment, personality is quantified in the parameter Tp. Tp is calculated as "Tp=Root (Sum over all Q (diff*importance)/# of Q's)".

The calculation for Tp proceeds as follows:

For all questions Q relating to personality, with response from a client as Rc and from a therapist as Rt, the root mean squared difference is:

$$\text{diff}=(Rc-Rt)^2$$

The importance is a measure of how strong the client's response is, thus how far away from the midpoint the slider is set, with some minimum importance value to not totally disregard midpoint values. Thus, the calculation utilizes the client's value minus the midpoint value 0.5 and then apply the Abs( ) function to remove any negation. The calculation then multiplies the result by 2 to provide a value for the importance in the range from 0 to 1. The calculation adds 1 to the intermediate result add 1 and divides this value by 2 to achieve a value for the importance in the range 0.5 to 1. In this calculation the minimum value for importance is 0.5, and as the slider is set further from the midpoint, the importance value goes towards 1.

$$\text{importance}=\text{Abs}(Rc-0.5)*2+1)/2$$

To complete the calculation, the formula then sums over all questions the difference multiplied by importance and divides the intermediate result by number of questions. The square root of this intermediate result is then calculated to arrive at the final value for Tp.

In an embodiment, the service outcome optimization system may calculate a value for self-reported issues/identities. The value, Ti, is calculated as:

$$Ti=\text{sum over all } L(Lc*Lt)/\text{sum over all } L(Lc)$$

Note: The service outcome optimization system may use the term "labels" in this description for self-reported issues/identities, such as, in a non-limiting example, self-reported 'transgender issues'. A therapist self-reports a label as a Boolean, such as, in a non-limiting example, an ability (or not) for dealing with transgender issues, where the existence of the ability is recorded as a 1 and not having the ability available is recorded as a 0.

In this algorithm, Lc is the label value of L for a client and Lt is the label value of L for a therapist. The values of L are in the range 0 to 1, for the therapist the value is Boolean, either a 0 or a 1. A client indicates in the range 0 to 1 how important each issue is to the client. The client input value for Lc is discretized as above between 0 and 1 in steps of 0.01.

The value of Ti is calculated as the product of Lc and Lt, multiplied by the sum of all values of L, divided by the product of Lc and the sum of all value of L. This provides a match score for the client and therapist for issue/identity requirements.

In an embodiment, the service outcome optimization system may measure competence in various ways, with varying assumptions. A simple way to measure competence of a therapist is to count the number of clients who show improvements in measurable outcomes. Each client fills out a check in and checkout form before and after each therapy session. For each question Q measuring clinical outcome, assuming a higher value means a better outcome, the service outcome optimization system can plot the responses for Q over time, where the time period may span from the initial session to the current session. The service outcome optimization system may then fit a line through the plot of the responses using simple linear regression. If the derivative of the line is non-trivially positive (i.e., the trend is upwards indicating improvement to some non-trivial degree), then we can count this as an outcome that is improving. The threshold of an identification of "trivial" in terms of improvement may be set by the user or may be established as a standard value by the service outcome optimization system against which the derivative of the line may be measured to determine if the threshold of non-trivial positive results has been met. The service outcome optimization system may sum the number of Qs that are improving divided by the number of Qs in total. This gives a measure for the improvement of a single client which the service outcome optimization system may then term fit. The service outcome optimization system may calculate the mean of all fits to arrive at a measure of competence. The calculation of competence, Tc, is thus expressed as:

$Tc$=sum for all therapist's clients (fit)/number of therapist's clients

The service outcome optimization system may calculate an overall match score for a client and a therapist. The overall match score between a client and a therapist is simply the mean of the three scores Tp, Ti and Tc:

Score=$(Tp+Ti+Tc)/3$

The service outcome optimization system may generate a list of therapists for the client to review. These therapists are ranked according to their match score with the client. These match scores are initially generated by the statistics based matching approach described above but will be replaced with a ML/deep learning approach once a sufficient amount of outcome data for training the ML/Deep Learning algorithms has been collected. The client is able to review profiles for each therapist before selecting a therapist to engage.

The client may meet the matched and selected therapist for a first interaction which would consist of a first service session. In a non-limiting example, service sessions are just one type of interaction that may take place between a customer and a service provider, such as, in this example, a client and a therapist. Before the session begins, the client and therapist are both required to complete a check in form. This check in form provides information about the client's treatment goals, and the client's and the therapist's subjective assessment of the client's mental health and progress towards any defined treatment goals.

After the interaction, labeled as a service session, ends the client and therapist are both required to complete a checkout form. This checkout form asks about the client and therapist's subjective assessment of the level of therapeutic alliance between the client and therapist during the interaction.

In an embodiment, the check in and checkout process steps are used before and after each session. Change in the calculated scores over time is an important signal of progress in therapy. In a non-limiting example, a successful match should demonstrate a pattern of decreasing scores on psychological distress measures during the check in and consistently high or moderate and increasing scores on measures of therapeutic alliance on the check out.

In an embodiment, upon the collection of a sufficient amount of outcome data from the check in and check out steps, where this data has been collected for many client-therapist pairs, the service outcome optimization system may evolve from a statistical-based matching approach to a deep learning approach through the application and use of machine Deep Learning algorithms. As the service outcome optimization system continues to collect more data it may use this information from the check ins and checkouts as training data to begin to teach the deep learning algorithm to better recognize matches to create better treatment outcomes and provide predictions and recommendations for such matches. The nonlinearity of matching and the discovery of previously unidentified latent, moderating and mediating variables is one way that the deep learning algorithm may discover as insights from the collected and analyzed data, rather than a simple AI/statistical matching algorithm where the assumption is more closely matched in terms of preferences and/or attributes. Nonlinear insights that result from the deep learning algorithm analysis means a better fit between clinicians and clients. In a non-limiting example, if a client indicates a preference for a therapist who is described as "challenging" instead of "supportive", the deep learning algorithm approach may identify that client who prefers a "challenging" therapist actually achieves better outcomes with a therapist who is described as "supportive." Furthermore, a deep learning algorithm approach may discover that the service outcome described above is actually moderated by another variable. In a non-limiting example, the deep learning algorithm approach may identify that a client who prefers a "challenging" therapist actually achieves better outcomes with a therapist who is described as "supportive," but only when the therapist is also described as "directive." Additionally, as the machine deep learning algorithms are provided with more data and human direction, the confidence in the recommendations presented by the service outcome optimization system will increase.

Crowdsourcing Profiles to Improve Accuracy of User Profiles.

In an embodiment, a process is described for crowdsourcing profiles to improve the accuracy of user profiles. This method augments and improves the accuracy of the core innovation by assuming that other service recipients are likely to provide a more useful assessment of a service professional's personality and areas of expertise than the professional is able to provide for themselves. The accuracy of these service recipient appraisals may be further improved by soliciting and collecting this feedback from many service recipients who have worked with the professional service provider to provide a more accurate appraisal. The accuracy of all user profiles may also be improved by soliciting and collecting feedback more generally from any individuals who have knowledge of a user's personality.

Using AI Methods for Insight Generation for Clinicians, Professionals, Educators, Salespersons and Other Service Providers.

The service outcome optimization system may use deep learning analysis to generate insights for use by clinicians and service provider professionals of all types. This approach is applicable to any relationship between a service provider and a service recipient where a fit between personality or preferences is key to achieving the partnership's desired outcomes. The process described provides service providers with insights into previously unidentified strengths or areas for growth. The supervision and feedback information provided to the service provider through the operation of deep learning analysis may also be used to augment traditional training or supervisory relationships for such professionals. Using the feedback and unique interpersonal insights provided by the process herein described, supervisory personnel may be better able to target training experiences to help the service provider to make improvements in any previously unidentified areas of weakness that may be due to lack of sufficient experience, lack of sufficient training, or areas of practice that are not preferred by the professional. The method also provides the service provider and supervisory personnel with direct feedback regarding the actual impact of professional development experiences through additional training, additional experience, or more judicial practice preferences on clinical outcomes and the professional-client relationship.

In an embodiment, a service provider may create a profile in the service outcome optimization system that is stored in an electronic data storage data file associated with the service provider. Upon the completion of a professional profile, the service provider may begin to meet with a variety of clients as recipients of the service providers professional services. In non-limiting examples, the clients may be adolescents, adults, young adults, elderly, or other age groups representing many different age groups and client types within each group.

In an embodiment, in addition to using these insights to guide the service outcome optimization system algorithm's future matching decisions, the professional service provider is also able to view these differences as areas of relative strength and weakness in the service provider's expertise. The service provider who performs significantly better with adults compared to adolescents as determined by service outcome optimization system analysis might decide to change the focus of their practice and how to present and advertise their practice so as to specialize with adult clients in order to maximize service outcome efficacy.

Supervisory guidance and direction may be enhanced by linking the professional's account with supervisory personnel. The link may provide supervisory personnel with insights into the professional's self-described areas of specialization and the specializations for which the professional may have a greater affinity.

In an embodiment, another important source of insight generation may come from the crowdsourcing of profiles as described earlier herein. These crowdsourced descriptions may be displayed and analyzed against the service provider's self-descriptions.

In an embodiment, over time the deep learning algorithm may begin to identify attributes that are consistently associated with treatment success. The nonlinearity of matching and latent variables are what the machine learning and deep learning algorithms may discover as insights from the collected and analyzed data, rather than a simple statistical matching algorithm where the assumption is more closely matched in terms of preferences and/or attributes. Insights derived as the nonlinear result from the deep learning algorithm analysis means a better fit between clinicians and clients. In a non-limiting example, if a score value of 0.5 represents a clinician that is equally a "thinker" and a "feeler" a score value of 0.75 would be representative of a clinician that is a moderately strong "feeler". In this non-limiting example, if the deep learning algorithm identifies that having a score of 0.75 is most highly correlated with successful treatment outcomes for a clinician, then Therapist scores above or below 0.75 on this attribute tend to be associated with less positive outcomes for the client. This information can then be used to guide a therapist's training and development. In this non-limiting example, a therapist with a score of 0.188 (this represents that clients strongly describe this clinician as "A Thinker") would benefit from learning to present themselves as more of "A Feeler." The therapist or supervisory personnel can use this information to construct data-driven training interventions. A data-driven intervention is based upon the nonlinear fit where the analysis of attribute data provides a result that is different or contrary to the fit of a match recommended by a simple AI/statistical matching algorithm. Conversely, a therapist who is strongly described as "A Feeler" (score=0.95) might benefit from training interventions that challenge them to present with a somewhat more analytical style with clients so as to bring the score closer to the attribute score of 0.75 as the optimum match fit score as discovered by the deep learning algorithm analysis.

In an embodiment, crowdsourced personality profiles from new clients can be used to provide feedback to a therapist and/or supervisory personnel regarding the success of any training intervention. In a non-limiting example, as previously described, a therapist with a 0.188 score might join an emotion-focused training group with the goal of learning to become more feelings-oriented to increase the score for that attribute from the value of 0.188 and move the attribute score closer to the optimum value of 0.75 as discovered by the deep learning algorithm analysis. After joining the emotion-focused training group, the therapist and/or supervisory personnel may be able to assess whether the training gained from the emotion-focused training group was an effective intervention. The effectiveness of the intervention may be quantified by comparing recently collected crowdsourced scores on this attribute with crowdsourced scores from a previous period in order to test whether there has been a statistically significant change in clients' perceptions of this attribute.

Using AI Methods for Insight Generation for Organizations Regarding Hiring Decisions.

The service outcome optimization system may provide organizations with deep insights into the latent preferences of the service recipients who are engaging with the organization as well as an assessment of how well the service providers within the organization are meeting these latent needs. Using the novel process as previously described herein, the system is able to identify the ideal service provider for the service recipient. Utilizing this process, insights generated through an analysis of attribute data through AI methods are also broadened to help an organization to make decisions regarding staffing needs. This process attempts to remove personal bias in hiring by first identifying the latent needs and preferences of incoming service recipients. Using this information, the algorithm is then able to identify the desired attributes of the perfect match for a service recipient. As the service outcome optimization system begins making matches the service outcome optimization system is also assessing how well the organization is able to provide a service provider who closely meets the needs of the service recipient from among the current pool of available service providers within the organization. This process, defined as "client-driven hiring", allows employers to make hiring decisions with increased confidence that these decisions have a high likelihood of improving the organization's ability to meet the needs of of their current and future service recipients, thereby improving the overall achievement of the desired outcomes for the organization. These desired outcomes include but are not limited to clinical improvement, client retention, increased sales, subject mastery, customer satisfaction.

In a non-limiting example, improving client/therapist interaction outcomes may require the acquisition or hiring of additional professional service providers through "client-based hiring". Any clients who do not generate a match score with any available therapists within the organization above a fixed threshold (best match score <70%) are classified as poorly matched. If, over time, the match score between the client and assigned professional therapist declines below the 70% threshold, or if there is no professional to assign to the client with a match score that meets or exceeds the match score threshold of 70%, the practice or organization may look to add therapists to meet the needs of those clients that are not well matched. These client profiles are set aside in a separate database. To identify and hire a professional that is better able to meet the needs of specific clients that are not yet well matched, the service outcome optimization system utilizes the set aside client profiles for specific match scores. The therapy outcome optimization system may compare client "perfect match" scores from the set aside client profiles with the actual scores of professionals under consideration for use in locating professionals that may meet the criteria of a fixed threshold for a match score above 70% for one or more clients to approach as new hires for the practice or organization.

In a non-limiting example, for the therapy outcome optimization system identifying poorly matched clients, it is important to begin generating insights about how an organization could expand the professional therapist team to provide better care to the full spectrum of clients seeking to engage the organization. To achieve better service outcomes, the therapy outcome optimization platform contains an analysis module that may calculate the mean score for each attribute preference among all poorly matched clients. This collection of mean preference scores represents an aggregate profile of all poorly matched clients.

In an embodiment, the practice administrator is able to log into the service outcome optimization system platform new hire portal and see a list of potential clinician new hires and view the profiles for these clinicians ranked based on the match scores between them and a collection of actual poorly matched clients or the degree of match between clinician applicants and the prototypical poorly matched client. Using these insights, the practice administrator is able to make data-driven hiring decisions that are most likely to improve the organization's ability to provide strong matches between all incoming clients and clinicians.

A Method for Distributing Referrals Based on the Latent Preferences of the Referral in Order to Improve Outcomes.

In an embodiment, the service outcome optimization system provides a novel process for using a AI approach to predict performance of a professional service provider based on the quality of the match between, a professional service provider and recipients of such professional services. This information can then also be used as a decision-making tool for distributing referrals within organizations, directories, etc. in order to optimize and maximize the desired outcome, where that outcome may include the non-limiting examples of clinical improvement, client satisfaction/retention or increased sales.

In an embodiment, matches between service providers and service recipients are traditionally made based on the overtly expressed needs and preferences of the service recipient and traditionally are distributed to clinicians based on these overtly expressed needs and preferences. Such needs and preferences may include: matching a client with a therapist based on scheduling availability (match with first available therapist), client needs with therapist expertise (a client seeking help with treatment for depression is matched with a therapist who specializes in depression), or the client or scheduler's subjective determination of a good match (client reads through a list of therapist bios and chooses a therapist). None of these traditional approaches harness the power of artificial intelligence to analyze past history, discover latent characteristics and preferences, identify non-linear relationships and produce recommendations based on these variables as well as the previous experience of similar clients to predict which therapist is likely to be most successful in generating the desired outcomes.

In an embodiment, using one or more deep learning algorithms becomes an important first intervention in the treatment of a client. Using the results from deep learning algorithm analysis for distributing referrals, also serves to help an organization, such as, in a non-limiting example, a group of therapists, to optimize their services in order to provide the best possible outcomes to the greatest number of clients. If a client is simply matched with an available therapist or allowed to select a therapist based only on their subjective assessment of a match, over time the distribution of clients within the organization will not be optimized.

In a non-limiting example, if clients are allowed to select a therapist without any recommendation data, these decisions may be influenced by factors that are not correlated with the desired outcomes such as page placement on a website or other publication, an engaging therapist biography, or an attractive headshot. The problem with decisions that are not supported or informed by recommendation data, is that the therapist who is at the top of the page and has an engaging bio and headshot will likely get matched frequently until they achieve a full caseload and are no longer able to take on any new clients. By using a recommendation system to help inform decision making, this process may reduce the influence of these extraneous influences and better distribute clients to therapists who are most likely to produce the desired or improved outcomes, thereby increasing the clinical efficacy of the entire organization.

A Method for Matching with a Unique Outcome Goal of Improving Mental Health and Emotional Wellbeing.

In an embodiment, this process involves an innovation in the goals of matching. Traditional goals of matching algorithms include: increasing sales, increasing customer satisfaction or increasing time spent on the platform. The method described below adds a unique goal of matching: customer wellbeing. Unlike customer satisfaction where the customer is satisfied and holds increasingly positive feelings towards the company or service that is performing the matching, customer wellbeing is focused on increasing the customer's satisfaction with their own life and positive feelings towards themselves and altruistic behaviors towards others.

Turning now to FIG. 1, this figure presents a flow diagram for matching a client with a professional service provider consistent with certain embodiments of the present invention. In an exemplary embodiment, at 100 the service outcome optimization system provides a client interface to permit a user to open and complete an intake questionnaire completing questions about demographics, issues and identities, and personality of the client. At 102 a professional service provider, such as in non-limiting examples, clinicians, salespersons, supervisory and administrative personnel, and other professionals, completes an intake questionnaire to select all concerns for which the therapist may have treatment experience and expertise. In a non-limiting example, a Therapist may be shown the prompt: "I would describe my therapeutic style as _____" and then also shown a slider with "Compassionate" on one end and "Challenging" on the other for entry of their response. All professional responses are retained in electronic storage files associated with each professional. At 104, the service outcome optimization system may compute a match score utilizing the intake parameters provided by the client, as well as a match score for each professional that has provided information on the intake questionnaire. At 106, the service outcome optimization system may then generate a ranked list of professionals where the ranking is based upon the match score generated for the professional. At 108, the client may select a professional from which to receive services from the ranked list presented to the client. At 110, the client and professional arrange for an initial session for service. If the initial session has not been arranged at 112, the service outcome optimization system will place the arrangement in wait mode until the client and professional have scheduled their initial session.

If, at 112, the initial session has been scheduled the service outcome optimization system at 114 will request the completion of a check-in form from the client to express the initial goals for the initial session activity. At 116, at the end of the initial session both the client and professional will complete a checkout form with session results. At 118, the checkout forms will be retained by the service outcome optimization system in an electronic storage file associated with the client and professional involved in the initial session. At 120, the Machine Learning (ML)/Deep Learning algorithm will be engaged to provide analysis of all collected data. At 122, the service outcome optimization system may provide match predictions for matches between clients and professionals based upon created match scores and provide users with recommendations on selection of professionals from whom they may seek services to achieve improved results.

Figure 2:
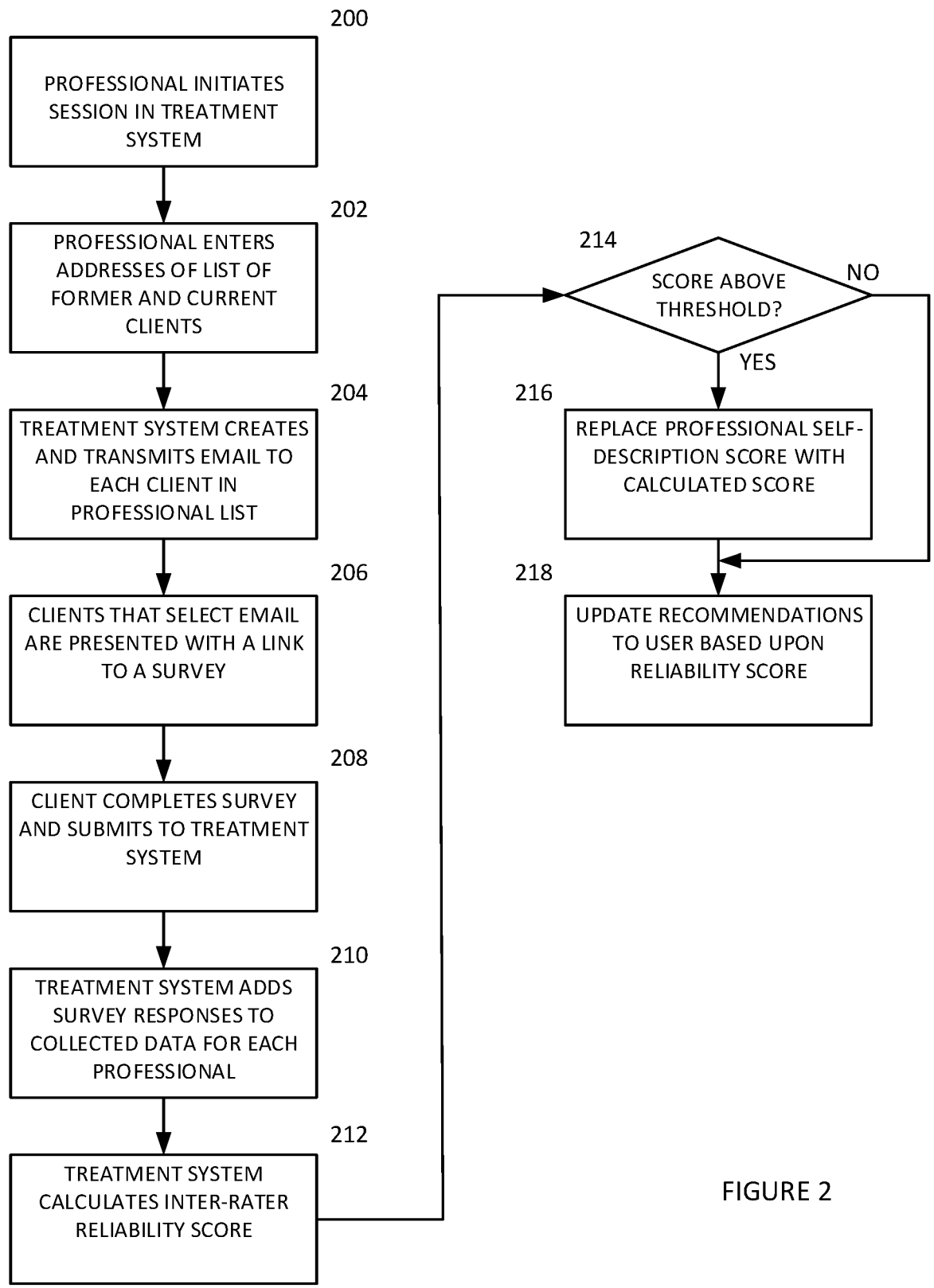
FIG. 2 is a flow diagram for improving user profiles using crowd sourced information consistent with certain embodiments of the present invention.

Turning now to FIG. 2, this figure presents a flow diagram for improving user profiles using crowd sourced information consistent with certain embodiments of the present invention. In an exemplary embodiment, a professional service provider such as, in a non-limiting example, a therapist or clinician as a user logs into the provided application through the application user interface of the service outcome optimization system at 200. The user is provided with an application screen to enter the email addresses of current and former clients who have retained the services of the clinician user at 202. The service outcome optimization system formulates and transmits to each current and former client identified a message to the email address provided by the clinician user at 204. The email message is formulated as an invitation that includes a link and an explanation of the value of providing honest feedback about the professional service provider to the service outcome optimization system. The link provided may supply the client with a survey form to be completed as feedback and uploaded to the service outcome optimization system. The purpose of the feedback information from the standpoint of the service outcome optimization system is not to evaluate the service provider but to help build a dataset of crowdsourced personality profile information for the service provider. A brief explanation of the types of questions that are asked in the survey form is provided as well as the estimated time to complete the survey. In an important note, the email to the client also explains that any information supplied in the survey as feedback will be anonymous.

In an embodiment, the client recipient of the email may click on the link and be presented with the survey of questions at 206. The survey provided by the service outcome optimization system may be short, but will present questions that are of most benefit in determining personality profile datapoints for the service provider that is the focus of the survey. In a non-limiting example, if the service provider is a therapist or clinician, a prompt for the survey questions may be of the form "I would describe Glenn's therapeutic style as _____", where 'Glenn' is the service provider who has caused the email to be sent to the client. This prompt may be followed by a series of semantic differential items. The questions are composed of two words or phrases that are somewhat opposing traits, but also are both generally considered to be positive or neutral personality attributes. In a non-limiting example, the two words may be presented as "A Thinker vs. a Feeler". Between the two words the client will see a slider. By moving the slider handle closer to one of the words, the client is indicating that this attribute more accurately describes the therapist. The slider represents a range of values from 0 to 1. In this non-limiting example, a 0 indicates that the respondent would strongly describe the clinician as "A Thinker" and a 1 indicates that the client would strongly describe the clinician as "A Feeler."

In an embodiment, at 208 upon completion, the client's answer to each question is added to a list of all responses that have been collected for each question at 210. In a non-limiting example, if three clients as respondents have strongly endorsed the description of the clinician as "A Thinker" (a=0, b=0, c=0) and one client respondent moderately endorses the description of the clinician as "A Feeler" (d=0.75), then the crowdsourced description of the clinician would be 0.188, which correlates more closely with the term "Thinker" than the term "Feeler". An inter-rater reliability score may also be calculated at 212. Upon reaching a pre-determined or input value for a specific threshold of interrater reliability (k>0.75) for an attribute, the platform will substitute this crowdsourced value (in this non-limiting example 0.188) for the value provided by the service provider's self-description.

At 214, the service outcome optimization system checks to determine if a newly calculated inter-rater reliability score is above the pre-set threshold of inter-rater reliability. If the new inter-rater reliability score is above the threshold, an existing attribute score for a service provider may be replaced with the newly calculated crowdsourced score at 216. If the new inter-rater reliability score is below the threshold, the service outcome optimization system does not replace the existing attribute score with the newly calculated attribute score that has been crowdsourced. At 218, the service outcome optimization system may update any recommendations to a user based upon the most current inter-rater reliability score.

In an embodiment, the substituted value for the service provider may be used in future calculations by the deep learning algorithms, herein previously described, as a datapoint to assist in the determination of prospective matches and future recommendations as well as a tool for generating insights for the users of the system.

Figure 3:
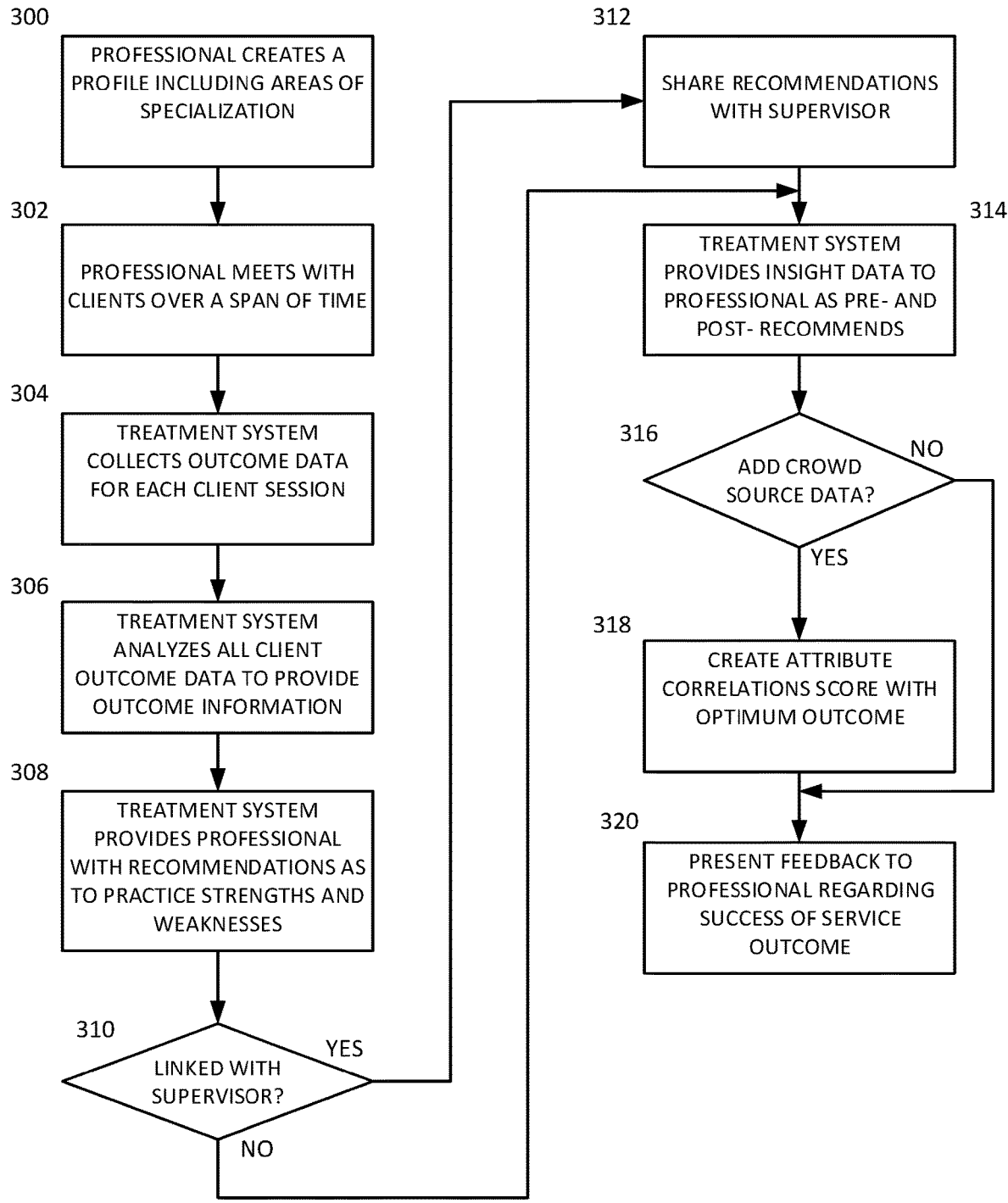
FIG. 3 is a flow diagram for insight generation using deep learning algorithm analysis consistent with certain embodiments of the present invention.

Turning now to FIG. 3, this figure presents a flow diagram for insight generation using deep learning algorithm analysis consistent with certain embodiments of the present invention. In an exemplary embodiment, a clinician or other professional may create a profile in the service outcome optimization system that is stored in an electronic data storage data file associated with the clinician or other professional. As part of creating this profile, the professional may include areas of specialization at 300. In a non-limiting example, a professional who is a therapist might have special expertise in working with a specific client population, such as adolescents.

At 302, the professional may meet with clients over time in a number of service sessions. At 304, over time the service outcome optimization system platform begins to collect outcome data on the success of the match as previously herein described. Upon collection of a sufficient amount of data from different clients to achieve statistical significance ($p<=0.05$), the service outcome optimization system platform is able to begin providing meaningful insights to the clinician professional regarding the professional's performance with different types of clients at 306. In a non-limiting example, while the clinician reported that they specialize in working with adolescents and may believe that their skill set is particularly suited for working with adolescents, upon statistical analysis by the service outcome optimization system, the platform may be able to demonstrate that the clinician has more desirable outcomes (for example, higher therapeutic alliance scores) among adults ($n=30$, $x\_bar=4.5$) when compared to adolescents ($n=45$, $x\_bar=3.1$).

In an embodiment, at 308 in addition to using these insights to guide the service outcome optimization system algorithm's future matching decisions, the clinician professional is also able to view these differences as areas of relative clinical strength and weakness. These insights may be used in a variety of different ways. In a non-limiting example, if a clinician is committed to working with a wide variety of types of clients and issues, then clinician may want to focus future training and supervision on improving outcomes among client groups for which the clinician may have underperforming statistics and analysis as compared to desired statistical outcomes with regard to improving clinical outcomes for those client groups. Alternatively, the clinician may use these insights to identify and develop a previously unidentified area of clinical strength. Using the previous example, the clinician professional who performs significantly better with adults compared to adolescents as determined by service outcome optimization system analysis might decide to change the focus of their clinical practice and how to present and advertise their practice so as to specialize with adult clients in order to maximize clinical efficacy.

At 310, if a professional's account is linked to a supervisor's account on the service outcome optimization system platform, then insights discovered through analysis of practice outcomes may also be shared with supervisory personnel at 312. By sharing these insights into a clinician's areas of clinical strength and weakness, supervisory personnel may be better able to assist in the development of more targeted training interventions. In a non-limiting example, the insight that the clinician is significantly better at connecting to adults as compared to adolescents, might lead to an exploration of why this might be the case. In this non-limiting example, perhaps the clinician, through self-reflection and conversations with their clients and supervisory personnel, realizes that they present in an overly formal way that is often interpreted as "fake" by many of their teenage clients. Supervisory personnel may craft interventions that help the clinician to become more spontaneous or explore traumatic experiences in their past that contribute to the clinician's fears about being more vulnerable and authentic, especially around adolescents. At 314, by sorting client outcome data from clients into two periods: pre-intervention and post-intervention, supervisory personnel and the clinician may be able to get direct feedback about the efficacy of the intervention. In this non-limiting example, after exploring the clinician's fears of being vulnerable with teenage clients, upon further analysis by the service outcome optimization system, utilizing additional clinical results as reported both by the clinician and the adolescent clients, the clinician may notice a statistically significant increase in reports of therapeutic alliance between the clinician and his or her adolescent clients.

At 316, another important source of insight generation may come from the crowdsourcing of profiles as described earlier herein. These crowdsourced descriptions may be displayed and analyzed against the therapist's self-descriptions. Any significant differences between these two scores may be highlighted through this comparison and correlations between an attribute score and an optimum outcome score at 318. The comparison and analysis may serve as a useful tool for insight generation for clinical professionals, helping them to more accurately understand how they are perceived by their clients.

At 320, the service outcome optimization system may present feedback to a professional regarding the success, or lack of success, of a service session outcome and present predictions and recommendations for the professional to act upon to update or modify the professional's areas of specialization. This modification of a professional's understanding of the areas in which the professional may have greater affinity may improve service outcomes over time.

Figure 4:
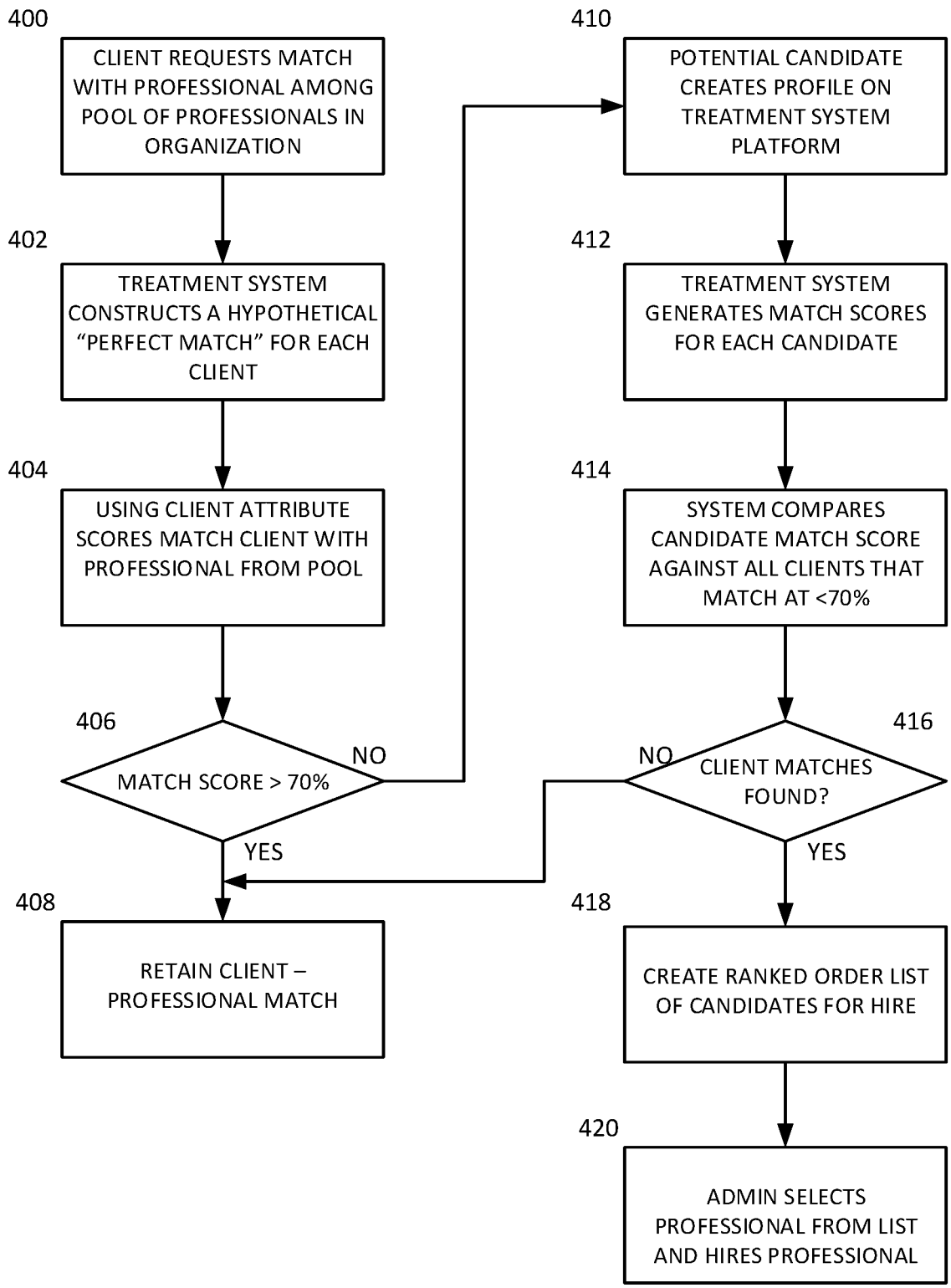
FIG. 4 is a flow diagram for the process of client-driven hiring consistent with certain embodiments of the present invention.

Turning now to FIG. 4, this figure presents a flow diagram for the process of client-driven hiring consistent with certain embodiments of the present invention. In an exemplary embodiment, the process of "client-driven hiring" as practiced by the service outcome optimization system begins when a new client requests a match with a professional at 400, such as, in a non-limiting example, a clinician, among a pool of available professionals within the organization. Using the client's expressed preferences as well as latent insights developed through the processes previously described herein, the platform is able to construct a hypothetical "perfect match" for the client at 402. The client may be matched with a professional within the organization as an initial match based upon the client input survey or other initial information provided to the organization whether or not the match score of the assigned professional meets the constructed hypothetical "perfect match" for this incoming client at 404. If the best match score for the professional matched to the client is above a minimum threshold, such as, in a non-limiting example, a match score above 70%, the client may be well matched with the professional assigned at 406.

To assess potential hiring decisions, potential professional clinician new hires, such as, in a non-limiting example, clinicians in a psychiatric services organization, are asked to create a profile on the service outcome optimization system platform through the new hire user interface at 408. Using the same process as previously described to generate match scores between a single client and a pool of professionals, such as clinicians, match scores are calculated between the organization's prototypical poorly matched client and the profile of each clinician applicant at 410. The clinicians with the highest match score are most likely to generate the desired outcomes with the organization's future poorly matched new clients, and, thus, are the most likely to be offered the opportunity to join the organization. At 414, the service outcome optimization system may compare candidate match scores against all client match scores that match professionals within the pool of the organization at less than 70%. At 416, the service outcome optimization system determines if any matches with current clients are found among the candidate profiles for incoming professionals. If client matches at or above 70% are found between clients and candidates, the service outcome optimization system places the candidate on a candidate for hire list at 418.

At 420, the practice administrator is able to log into the service outcome optimization system platform new hire portal and see a list of potential clinician new hires and view the profiles for these clinicians ranked based on the match scores between them and the prototypical poorly matched client. Using these insights, the practice administrator is able to make data-driven hiring decisions that are most likely to improve the organization's ability to provide strong matches between all incoming clients and the organization's pool of clinicians.

Figure 5:
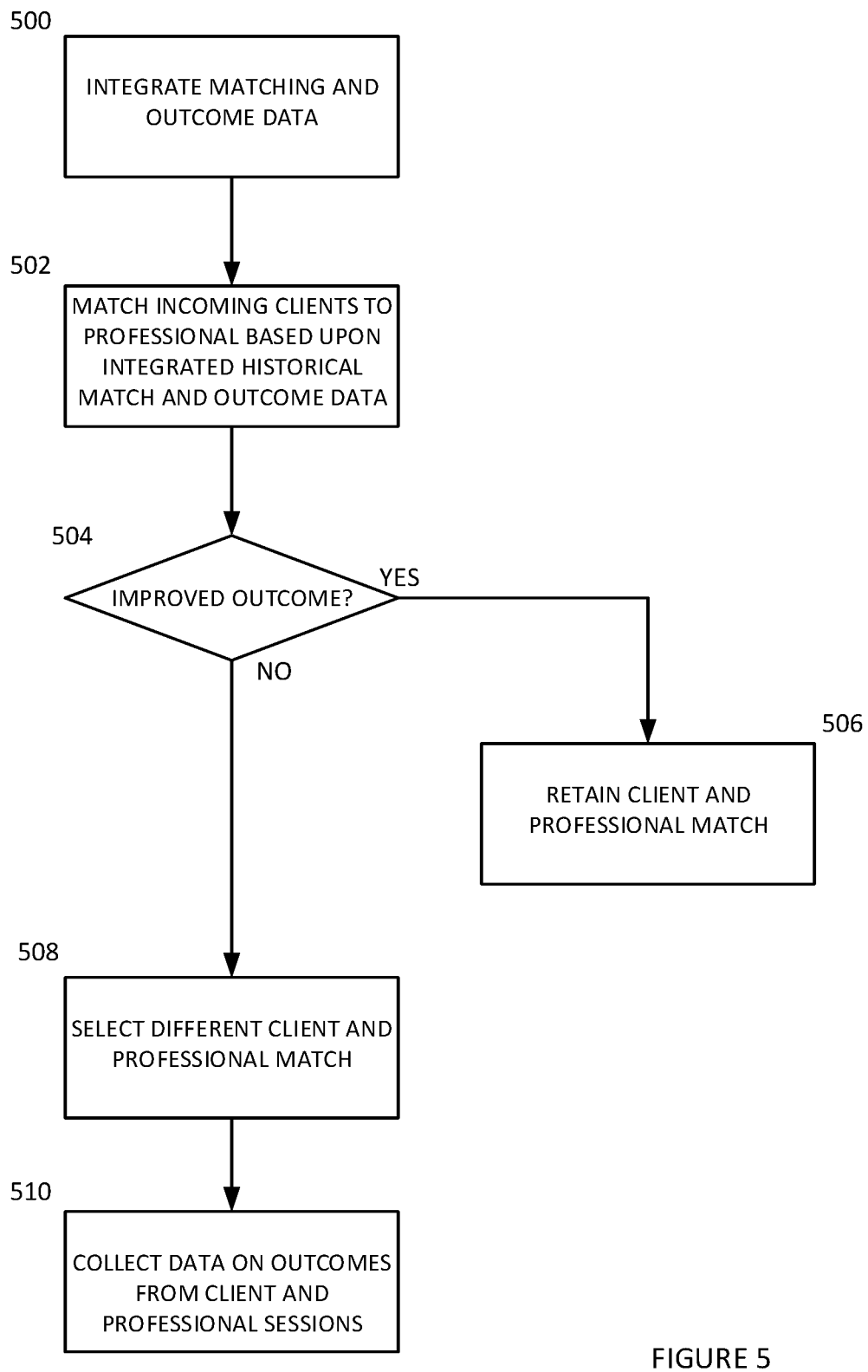
FIG. 5 is a flow diagram for optimizing service outcomes through better matching between a client and a professional, or a professional and an organization consistent with certain embodiments of the present invention.

Turning now to FIG. 5, this figure presents a flow diagram for optimizing service outcomes through better matching between a client and a professional, or a professional and an organization consistent with certain embodiments of the present invention. In this embodiment, at 500 an organization decides to integrate the matching and outcome measurement technology as herein previously described. At 502, incoming clients are matched with therapists within the organization based on recommendations from a ML/deep learning algorithm that has been trained on data collected from past clients. At 504, the service outcome optimization system reviews the client and professional pairings to determine if improved session outcomes are observed from session surveys. At 506, if improvement in outcomes is observed, the client and professional match is retained.

If, however, improvement in outcomes or a decline in outcomes is observed at 508 the redistribution of clients who are already matched with a therapist to a new therapist is facilitated in order to further optimize an organization's ability to produce the highest outcomes among the largest number of clients. To accomplish this, at 510 the platform collects data about a client's clinical improvement over time as well as the client's rating of the current match or fit between client and therapist. If the platform detects a poor fit, the client is able to match with a new therapist and this new information about a poor fit between the client and therapist is taken into account when recommending a new match for the client.

Figure 6:
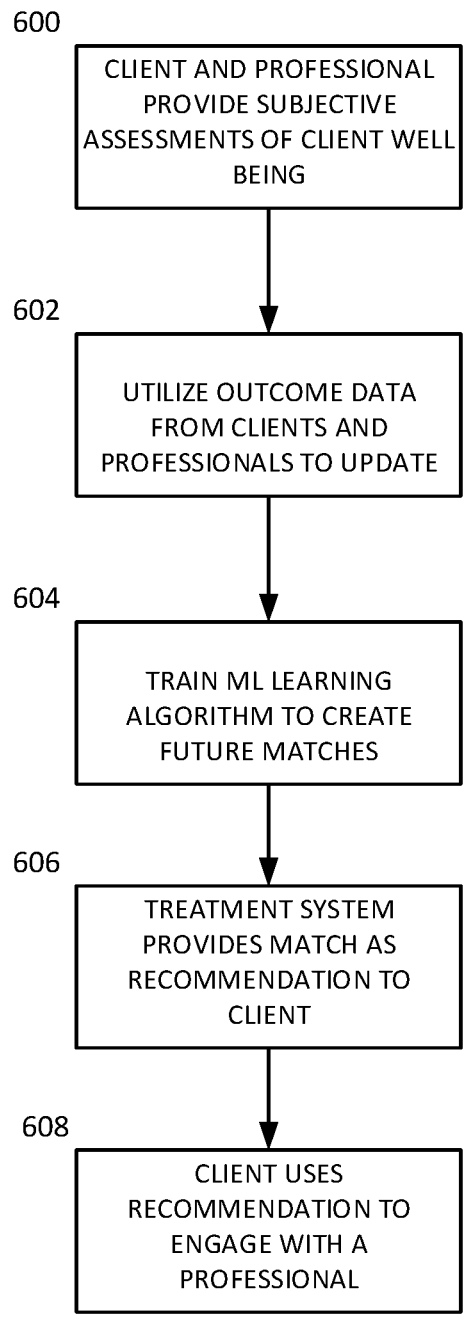
FIG. 6 is a flow diagram for matching to improve service outcomes utilizing deep learning algorithm analysis consistent with certain embodiments of the present invention.

Turning now to FIG. 6, this figure presents a flow diagram for matching to improve service outcomes utilizing deep learning algorithm analysis consistent with certain embodiments of the present invention. In this embodiment, at 600 during the check in and check out process outlined as previously described, the client and therapist will be asked to provide subjective assessments of the client's wellbeing. At 602, these assessments include but are not limited to questions assessing mental health status, life satisfaction and hope regarding the future.

At 604, using the same process as previously described, this outcome data is used to "train" the deep learning algorithm to match future clients and therapists in order to maximize client wellbeing outcomes. To improve treatment outcomes at 606, the service outcome optimization system may provide one or more matches of clients to professional service providers based upon the recommendations from the deep learning algorithm analysis. At 608, the client may then use the recommendation from the service outcome optimization system to engage with a professional to improve the match decision making process and, subsequently, improve the treatment outcome experienced by the client.

While certain illustrative embodiments have been described, it is evident that many alternatives, modifications, permutations and variations will become apparent to those skilled in the art in light of the foregoing description.

What is claimed is:
1. A method for predictive matching, comprising:
a service outcome optimization system collecting intake information comprising input personality scores, issue/identity scores, and therapist competence scores from one or more clients and one or more service providers;
computing a client match score for each of said clients and computing a service provider match score for each of said service providers utilizing said intake information;
comparing each of said client match scores against each of said service provider match scores to determine the match score value difference between each of said client match scores against each of said service provider match scores;
storing each match score value difference that has a value greater than or equal to a pre-established minimum as a best match score for each client and service provider pair;
creating a ranking list of service providers ranked according to said one or more stored best match scores for each service provider and client pair and presenting said ranking list of service providers to said one or more clients;
said one or more clients engaging a service provider from said ranking list and completing at least one interaction with said engaged service provider;
collecting results data from all interactions with each of said engaged service providers;
providing said intake information and said results data to a machine learning algorithm as training data to permit said machine learning algorithm to recognize client and service provider matching that meet a client expressed outcome;
said machine learning algorithm identifying nonlinear matches where previously unidentified latent, moderating and mediating variables permit said nonlinear matches to optimize a client expressed outcome regardless of a best match score value;
utilizing one or more nonlinear match predictions from said machine learning algorithm to provide recommendations to said one or more clients for engaging future service sessions with said one or more service providers.

2. A method according to claim 1 further comprising said intake information from one or more clients consisting of intake questionnaires.

3. A method according to claim 2, where said intake information comprises demographics, issues, identities, and personality information about said one or more clients.

4. A method according to claim 1 further comprising intake information from one or more service providers consisting of intake questionnaires.

5. A method according to claim 1, where said match score is computed utilizing said intake information from said one or more clients and said one or more service providers.

6. A method according to claim 1, where said service session is an initial session with said selected service provider.

7. A method according to claim 6, where said service session begins with the completion of a check-in form with stated initial goals for said service session providing the start plan from the client to said service provider for results expected by said client from said service session.

8. A method according to claim 1, where each interaction requires the completion by said client of a check-out form stating the results experienced from said interaction.

9. A method according to claim 1, where said service outcome optimization system collects all check-in and check-out information, stores all collected information into an electronic storage device, and transmits all collected information to one or more analytical learning components in said service outcome optimization system.

10. A method according to claim 1, where said match predictions and/or recommendations are provided as results from an analysis by said analytical learning components of said all collected information.

11. A system for predictive matching, comprising:
a server comprising a data processor;
said data processor comprising a service outcome optimization system collecting intake information comprising input personality scores, issue/identity scores, and therapist competence scores from one or more clients and one or more service providers;
said data processor computing match score for each of said clients and computing a service provider match score for each of said service providers utilizing said intake information;
said data processor comparing each of said client match scores against each of said service provider match scores to determine the match score value difference between each of said client match scores against each of said service provider match scores;
said data processor storing each match score value difference that has a value greater than or equal to a pre-established minimum as a best match score for each client and service provider pair;
said data processor creating a ranking list of service providers ranked according to said one or more stored best match scores for each service provider and client pair and presenting said ranking list of service providers to said one or more clients;
said one or more clients operating a user interface within said data processor to engage a service provider from said ranking list and completing at least one service session with said engaged service provider;
said service outcome optimization system collecting results data from all interactions with each of said service providers;
said service outcome optimization system providing said intake information and said results data to a machine learning algorithm as training data to permit said machine learning algorithm to recognize client and service provider matching that meet a client expressed outcome;
said machine learning algorithm identifying nonlinear matches where previously unidentified latent, moderating and mediating variables permit said nonlinear matches to optimize a client expressed outcome regardless of a best match score value;
said service outcome optimization system utilizing one or more nonlinear match predictions from said machine learning algorithm to provide recommendations to said one or more clients for engaging future service sessions with said one or more service providers.

12. A system according to claim 11 further comprising said intake information from one or more clients consisting of intake questionnaires.

13. A system according to claim 12, where said intake information comprises demographics, issues, identities, and personality information about said one or more clients.

14. A system according to claim 11 further comprising intake information from one or more service providers consisting of intake questionnaires.

15. A system according to claim 11, where said match score is calculated by said data processor and is computed utilizing said intake information from said one or more clients.

16. A system according to claim 11, where said service session is an initial session with said selected service provider.

17. A system according to claim 16, where said service session begins with the completion of a check-in form with stated initial goals for said service session providing the start plan from the client to said service provider for results expected by said client from said service session.

18. A system according to claim 11, where each service session requires the completion by said client of a check-out form stating session results.

19. A system according to claim 11, where said service outcome optimization system collects all check-in and check-out information, stores all collected information into an electronic storage device, and transmits all collected information to one or more machine language learning components in said service outcome optimization system.

20. A system according to claim 11, where said match predictions and/or recommendations are provided by said service outcome optimization system as results from an analysis by said machine language learning components of said all collected information.

* * * * *